United States Patent
Brown

(10) Patent No.: US 6,395,290 B2
(45) Date of Patent: May 28, 2002

(54) SUSTAINED RELEASE ANIMAL REPELLENTS

(75) Inventor: Larry R. Brown, 25 Sumner St., Newton, MA (US) 02459

(73) Assignees: Larry R. Brown, Newton; Robert I. Kahn, Newton Centre, both of MA (US)

( * ) Notice: Subject to any disclaimer, the term of this patent is extended or adjusted under 35 U.S.C. 154(b) by 0 days.

(21) Appl. No.: 09/130,677

(22) Filed: Aug. 6, 1998

Related U.S. Application Data
(60) Provisional application No. 60/054,994, filed on Aug. 6, 1997.

(51) Int. Cl.[7] ............................................. A01N 25/10
(52) U.S. Cl. ................... 424/408; 424/409; 424/411; 424/417; 424/484; 424/486; 574/675; 574/920; 523/122
(58) Field of Search .................. 523/122; 424/405–409, 424/417–420, 484–488, 411; 514/675, 920

(56) References Cited

U.S. PATENT DOCUMENTS

| | | | | |
|---|---|---|---|---|
| 676,375 A | * | 6/1901 | Whipple | 424/403 |
| 3,474,176 A | * | 10/1969 | Freeman | 424/331 |
| 3,857,934 A | | 12/1974 | Bernstein et al. | |
| 4,247,498 A | * | 1/1981 | Castro | 264/41 |
| 4,548,764 A | * | 10/1985 | Munteanu et al. | 261/75 |
| 4,554,155 A | * | 11/1985 | Allan et al. | 424/22 |
| 4,555,015 A | | 11/1985 | Haase | |
| 4,562,794 A | | 1/1986 | Speckman | |
| 4,767,812 A | * | 8/1988 | Chapin et al. | 524/144 |
| 4,775,532 A | | 10/1988 | Clayton | |
| 4,855,127 A | * | 8/1989 | Abrutyn et al. | 424/411 |
| 5,017,377 A | | 5/1991 | Sikinami et al. | |
| 5,019,400 A | | 5/1991 | Gombotz et al. | |
| 5,281,621 A | * | 1/1994 | Wilson et al. | 574/459 |
| 5,698,209 A | * | 12/1997 | Shono et al. | 424/405 |

* cited by examiner

*Primary Examiner*—Neil S. Levy
(74) *Attorney, Agent, or Firm*—Fish & Richardson P.C.

(57) ABSTRACT

Compositions and methods for repelling an animal from an area or object are described. The compositions include an animal repellent dissolved or dispersed in a polymer where the repellent is released from the polymer over a period of time in an amount effective to repel an animal from the area. Capture of the repellent in the polymeric matrix allows for concentration of the repellent in an easily movable or removable device. Moreover, the repellent is not diluted by contact with water. The composition is provided in a usable form as a film, a sheet, a shaped article, pellets, or microparticles. The method for repelling an animal from an area or object includes preparing a device incorporating the above compositions and placing the device in an area or near or on an object desired to be protected. The devices can be manufactured by solvent evaporation, solvent removal, coextrusion, spray drying, and hot melt encapsulation. In a preferred embodiment the polymer is ethylene vinyl acetate copolymer and the repellent is methyl nonyl ketone or animal predator urine.

3 Claims, 1 Drawing Sheet

SUSTAINED RELEASE OF METHYL NONYL KETONE FROM EVAc COPOLYMER MATRICES AS A FUNCTION OF WEIGHT PERCENT LOADING

SUSTAINED RELEASE ANIMAL REPELLENTS

CROSS REFERENCE TO RELATED APPLICATION

The present application claims priority to provisional patent application Ser. No. 60/054,994, filed on Aug. 6, 1997.

FIELD OF THE INVENTION

The present invention is in the field of methods and compositions for repelling animals.

BACKGROUND OF THE INVENTION

For many reasons, including health and safety related reasons, people often desire to repel animals from a particular area or object. For example, in urban, suburban, and rural regions frequented by wild animals, such as raccoons, squirrels, etc., it is often a problem that the animals will disrupt garbage cans and other refuse receptacles, leading to refuse strewn over the ground. This problem is also commonly faced in areas where domesticated animals are allowed to roam unattended. It is also often desired to repel domesticated animals such as dogs and cats from household areas or objects such as a couch.

Methyl nonyl ketone is presently used as a dog and cat repellent/training aid and as an iris borer deterrent in residential households and dwellings, on outdoor paths and patios, in solid waste containers, with ornamental and shade trees, ornamental herbaceous plants, ornamental lawns, and with ornamental woody shrubs and vines such as around perimeters of vegetable plantings. U.S. Pat. No. 4,775,532 discloses a liquid composition of methyl nonyl ketone and di(alkyl)adipate for use in repelling and training dogs and cats.

Methyl nonyl ketone is generally formulated as a pressurized liquid, as a ready-to-use liquid in a pump/sprayer device, or as a solid granular or crystalline formulation. The liquid formulations contain about 1.9% methyl nonyl ketone and about 0.1% related compounds. Various solid formulations are available as 1.9% methyl nonyl ketone and 0.1% related compounds, 0.08% methyl nonyl ketone and 0.42% cinnamaldehyde, or 6.25% thiram, 6.25% methyl nonyl ketone and 5.50% castor oil.

Methods of application of the preparations presently used include spreading the granular or crystalline formulation onto soil or ground as a border treatment, between rows of plants, or around the base of ornamental plants and objects. The pressurized liquid or liquid ready-to-use formulations are applied to the bark of trees and base of shrubs. For surface and indoor treatments, a piece of cloth can be sprayed and attached to the item to be protected.

The pressurized liquid or ready-to-use liquid products reportedly repels cats and dogs for about 12 to 14 hours following application. Repeat application is recommended after rain.

Many users claim that the presently available formulations of methyl nonyl ketone do not function effectively to repel animals. Short duration of repellency and low concentration of repellent in the vicinity of the item or area to be protected are reasons cited for ineffectiveness.

The application of methyl nonyl ketone upon surfaces and objects presents many problems. The chemical cannot be applied directly to ornamental or other plants because vegetation may be damaged. The use of methyl nonyl ketone in commercial food processing or preparation areas is not recommended nor is the application of methyl nonyl ketone to food crops or to soft stemmed bodied plants or application directly to water. Pressurized liquid and liquid ready-to-use formulations may stain or soften some fabrics or plastics.

It is therefore an object of the present invention to provide a self contained composition which provides controlled release of animal repellent over a period of time.

BRIEF SUMMARY OF THE INVENTION

Compositions and methods for repelling an animal from an area or object are described. The compositions include an animal repellent dissolved or dispersed in a polymer where the repellent is released from the polymer over a period of time in an amount effective to repel an animal from the area. Capture of the repellent in the polymeric matrix allows for concentration of the repellent in an easily movable or removable device. Moreover, the repellent is not diluted by contact with water.

In a preferred embodiment the polymer is ethylene vinyl acetate copolymer and the repellent is methyl nonyl ketone or animal predator urine. The composition is provided as a film, a sheet, a shaped article, pellets, or microparticles.

The method for repelling an animal from an area or object includes preparing a device incorporating a composition as described above and placing the device in an area or near or on an object desired to be protected. The devices can be manufactured by various methods such as solvent evaporation, solvent removal, diffusion into preformed matrices, coextrusion, spray drying, and hot melt encapsulation.

DETAILED DESCRIPTION OF THE INVENTION

Figure 1:
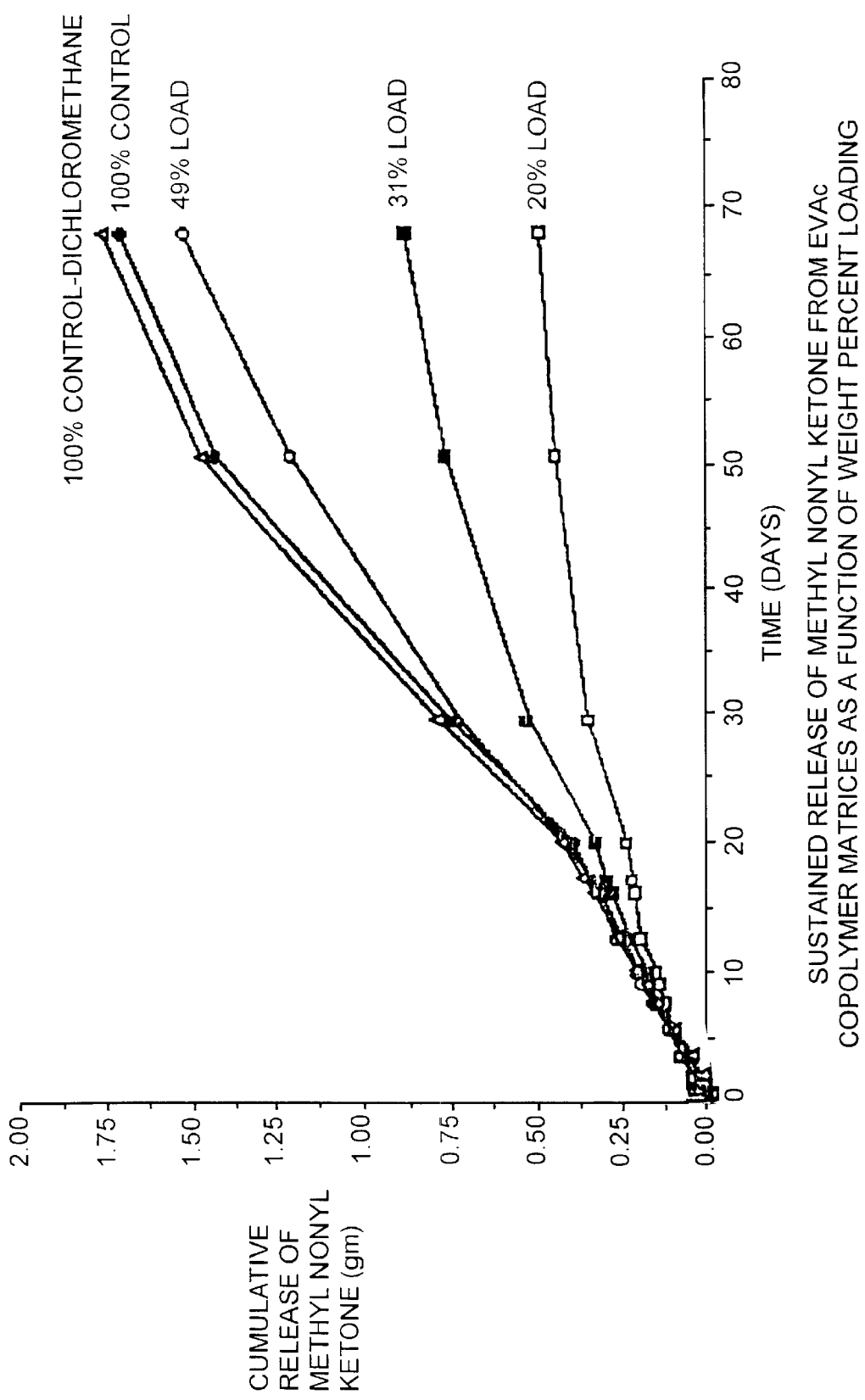
FIG. 1 illustrates sustained release of methyl nonyl ketone from EVAc copolymer matrices as a function of weight percent loading, where □ indicates 20% loading (w/w), ■ indicates 31% loading (w/w), ○ indicates 49% loading (w/w), ● indicates control of no polymer, and Δ indicates control of no polymer and no solvent.

Controlled release formulations in polymeric vehicles have been used for delivery of pesticides, insecticides, fertilizer, detergents, perfumes and in drug delivery. U.S. Pat. No. 5,017,377 to Sikinama et al. discloses a controlled release insect pest repellent including p-menthane-3,8-diol blended with an ethylene vinyl acetate copolymer.

Controlled release formulations can be formulated using either non-degradable or degradable polymeric materials. In one type of polymeric delivery system, a polymeric capsule is formed around or incorporating the agent to be delivered. The type of agent being delivered and the environment in which the agent is intended to be used determine the composition of the polymer or polymers used and the method that can be used to incorporate the agent. Alternatively, the polymer can be in the form of a sheet, pellets, a film, or a shaped article.

Unlike the uncontrolled application of repellents such as methyl nonyl ketone in the presently marketed forms, in the present device and method the repellent is released from the polymeric compositions in a controlled manner for a longer time period and at a sustained effective repellent concentration. Controlled release devices are disclosed which can be placed and/or affixed where desired, moved around, and removed when desired. Continuous release of repellent is provided over a several week time period and the repellent is protected from environmental elements such as rain without the need for reapplication. In addition, the device can be fabricated so that release only occurs from a single surface of the device, allowing it to be placed on or adjacent to ornamental plants and/or vegetation without damaging the plant.

In one embodiment, the composition is a polymeric film that incorporates methyl nonyl ketone therewithin. In another embodiment, the composition is a polymeric film containing an environmentally inert and safe repellent such as predator's urine.

A. Compositions

The compositions are made from a polymer and an animal repellent. The compositions may be manufactured as devices such as shaped articles, films, sheets, pellets, or microparticles.

Repellents

Methyl nonyl ketone, also known as 2-undecanone, and related chemicals known to act to repel animals can be used. Alternatively, or in addition, other repellents can be used such as those contained in the urine of various predators to the animals one wants to repel. For example, fox urine can be used, as foxes are known predators to squirrels, rabbits, deer, woodchucks, raccoons, chipmunks and other varmints. Coyote urine and bobcat urine can be used, as coyotes and bobcats are known predators to mice, moles and deer. Wolf urine can also be used, as wolves are predators to moose, coyote and bears. These repellents can be used as urine or as an isolated or synthesized form of chemicals contained in the urine and can be used in lyophilized form.

Other repellents include N,N-diethyltoluamide (DEET), cinnamaldehyde, thiram, capsicum, and quinine. The method and materials described herein are not limited to any particular repellent but are applicable to any which can be incorporated into a sustained release matrix as described herein. Preferred compounds are hydrophilic, lipophilic, or particulate in form, such as aliphatic or aromatic compounds possessing repellent properties.

Polymers

A number of polymers can be used. The polymer must be compatible with the repellent and able to release the repellent over time, such as by degradation of the polymer. The polymer itself should not have detrimental effects on the area or object with which it is to be used, such as foliage if the composition is to be applied directly to plants. Preferably, the polymer is not water soluble or is only marginally water soluble and there is minimal leeching of the repellent out of the composition upon contact with water.

A preferred polymer is ethylene vinyl acetate (EVAc) because it is compatible with aliphatic and aromatic compounds such as methyl nonyl ketone. EVAc yields a homogenous, flexible film which is compliant and can possess adhesive qualities. EVAc is hydrophobic which protects the incorporated repellent from leaching. Examples of other polymers and classes of polymers which can be used include poly(ethylene), poly(propylene), polyvinyl polymers such as poly(vinyl chloride), polyesters such as polylactide and polyglycolide and copolymers and mixtures thereof, poly orthoesters, polysaccharides such as dextran, dextran sulfate, cellulose, starches, acid hydrolyzed hydroxypropyl ether starches, polyurethanes, poly(anhydrides), poly(carbonates), poly(acrylates), poly(butadienes), fluoropolymers, poly(acryonitriles), poly(vinyl acetate), poly(methyl methacrylate), poly(styrene), poly(oxymethylene), poly(oxyethylene-oxyterephthaloyl), poly(ethylene terephthalate), poly(amides), polymers containing cyclic groups and aromatic polymers, and polyamino acids such as polylysine and polyarginine.

B. Methods for making the compositions

The concentration of repellent in the matrix can range from 10% to 90% by weight, preferably between 20% and 80%, most preferably between about 30% and 70%.

The polymeric compositions incorporating the repellent can be produced by a number of techniques, depending upon the polymer and the nature of the desired composition. For shaped articles, pellets, films and sheets, preferred methods are solvent evaporation and coextrusion of the repellent and polymer. Particles can be produced using solvent evaporation, spray drying, solvent removal, and hot melt encapsulation, as discussed below.

Shaped Articles, Pellets, Films and Sheets

Solvent Evaporation. In this method the polymer is dissolved in a volatile organic solvent such as methylene chloride. The repellent is added to the polymer solution and the combination is mixed. The mixture is poured into a mold or other receptacle having the desired shape and size, and the solvent is evaporated from the mixture.

Co-Extrusion. In this method, the polymer is granulated and melted. The repellent is added and mixed with the polymer and the combination is extruded through an injection molder such as a twin screw extrusion device. A plasticizer such as di(n-butyl)-o-phthalate, di(n-dodecyl)-o-phthalate, di(n-ethyl)-o-phthalate, di(n-heptyl)-o-phthalate, di(n-methyl)-o-phthalate, di(n-nonyl)-o-phthalate, di(n-propyl)-o-phthalate, or tricresyl phosphate can be added to lower the melting point of the polymer, allowing it to be extruded at a lower temperature. An important advantage of co-extrusion is that an organic solvent is not required.

Particles

Solvent Evaporation. In this method the polymer is dissolved in a volatile organic solvent such as methylene chloride. The repellent is added to the polymer solution and the combination is mixed. The mixture is sonicated or homogenized and the resulting dispersion or emulsion is added to an aqueous solution that contains a surface active agent such as TWEEN™ 20, TWEEN™ 80, PEG or poly(vinyl alcohol) and homogenized to form an emulsion. The resulting emulsion is stirred until most of the organic solvent evaporates, leaving microparticles. Several different polymer concentrations can be used between about 0.05 to 0.60 g/ml. Microparticles with different sizes, from about 1 to 1000 microns, and morphologies can be obtained by this method. This method is useful for relatively stable polymers like polyesters.

Solvent evaporation is described by E. Mathiowitz, et al., *J. Scanning Microscopy*, 4, 329 (1990); L. R. Beck, et al., *Fertil. Steril.*, 31, 545 (1979); and S. Benita, et al., *J. Pharm. Sci.*, 73, 1721 (1984), the teachings of which are incorporated herein.

Labile polymers, such as polyanhydrides, may degrade during this fabrication process due to the presence of water. For these polymers, the following two methods, which are performed in completely organic solvents, are more useful.

Hot Melt Microencapsulation. In this method, the polymer is first melted and then mixed with the repellent. The mixture is suspended in a non-miscible solvent (like silicon oil), and, while stirring continuously, heated to 5° C. above the melting point of the polymer. Once the emulsion is stabilized, it is cooled until the polymer particles solidify. The resulting microparticles are washed by decantation with a polymer non-solvent such as petroleum ether to give a free-flowing powder. Microparticles with sizes between one to 1000 microns can be obtained with this method. The external surfaces of particles prepared with this technique are usually smooth and dense. This procedure is used to prepare microparticles made of polyesters and polyanhydrides. However, this method is limited to polymers with molecular weights between about 1000 to 50,000.

Hot-melt microencapsulation is described by E. Mathiowitz, et al., *Reactive Polymers*, 6, 275 (1987), the teachings of which are incorporated herein. Polyanhydrides, for example, made of bis-carboxyphenoxypropane and sebacic acid with molar ratio of 20:80 (P(CPP-SA) 20:80) (Mw 20,000), can be prepared by hot-melt microencapsulation or for example, poly(fumaric-co-sebacic) (20:80) (Mw 15,000) microparticles can be prepared by hot-melt microencapsulation.

Solvent Removal. This technique was primarily designed for polyanhydrides. In this method, the repellent is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. The external morphology of particles produced with this technique is highly dependent on the type of polymer used.

Spray Drying of Microparticles. Microparticles can be produced by spray drying by dissolving a biocompatible polymer in an appropriate solvent, dispersing the repellent into the polymer solution, and then spray drying the polymer solution, to form microparticles. As defined herein, the process of "spray drying" a solution of a polymer and a repellent refers to a process wherein the solution is atomized to form a fine mist and dried by direct contact with hot carrier gases. Using spray drying apparatus available in the art, the polymer solution may be delivered through the inlet port of the spray drier, passed through a tube within the drier and then atomized through the outlet port. The temperature may be varied depending on the gas or polymer used. The temperature of the inlet and outlet ports can be controlled to produce the desired products.

The size of the particulates of polymer solution is a function of the nozzle used to spray the polymer solution, nozzle pressure, the flow rate, the polymer used, the polymer concentration, the type of solvent and the temperature of spraying (both inlet and outlet temperature) and the molecular weight. Generally, the higher the molecular weight, the larger the particle size, assuming the concentration is the same. Typical process parameters for spray drying are as follows: polymer concentration=0.005–0.20 g/ml, inlet temperature=30–1000° C., outlet temperature=20–100° C., polymer flow rate=5–200 ml/min., and nozzle diameter= 0.2–4 mm ID. Microparticles ranging in diameter between one and ten microns can be obtained with a morphology which depends on the selection of polymer, concentration, molecular weight and spray flow.

Hydrogel Microparticles. Microparticles made of gel-type polymers, such as polyphosphazene or polymethylmethacrylate, are produced by dissolving the polymer in an aqueous solution, if desired suspending a repellent in the mixture, homogenizing the mixture, and extruding the material through a microdroplet forming device, producing microdroplets which fall into a hardening bath consisting of an oppositely charged ion or polyelectrolyte solution, that is slowly stirred. The advantage of this technique is the ability to further modify the surface of the microparticles by coating them with polycationic polymers, such as polylysine, after fabrication. Microparticle sizes are controlled by using various size extruders.

Solvents

As defined herein, the polymer solvent is an organic solvent that is volatile or has a relatively low boiling point or can be removed under vacuum, such as dichloromethane (methylene chloride). Other solvents, such as ethyl acetate, ethanol, methanol, dimethyl formamide (DMF), acetone, acetonitrile, tetrahydrofuran (THF), acetic acid, dimethyl sulfoxide (DMSO) and chloroform also may be utilized, or combinations thereof. In general the polymer is dissolved in the solvent to form a polymer solution. When EVAc is the polymer, for example, the repellent can be at a concentration of between about 5% and 40% weight to volume (w/v), more preferably between about 10% and 20% w/v.

C. Methods for using the devices

The devices are placed in desired locations such as on the side, top, or inside a garbage can, around the base of a tree, or on top of or under a piece of furniture. The devices can also be directly attached to an object or area to be protected.

When the compositions are formulated as microspheres they can be widely distributed across an area to be protected by using a spreader, for example. Other means of dispersion can also be used as well as direct application by shaking or pouring the particles onto the desired area.

EXAMPLES

The compositions and methods described herein will be better understood with reference to the following non-limiting examples.

Materials

Ethylene vinyl acetate copolymer was obtained from USI Vynathene Quantum Chemicals under the tradename USI VYNATHENE™. Methyl nonyl ketone was obtained from Acros Chemicals. Coyote and bobcat urine were obtained from Foggy Mountain, DG-100, J&C MK, Hampden, Me. L101 Pluronic was obtained from BASF Corporation, Parsipanny, N.J. Pure Cote B790 food starch was obtained from Grain Processing Corporation, Muscatine Iowa.

Example 1

Polymeric Sheet Containing Methyl Nonyl Ketone

Ten (10) grams of ethylene vinyl acetate copolymer (EVAc), 40% vinyl acetate by weight, was dissolved in a total volume of 100 ml dichloromethane. The copolymer was allowed to dissolve over a 16 hour period in order to create a 10% (wt/vol.) solution of the polymer in dichloromethane. Ten (10) grams of methyl nonyl ketone was added to the polymer solution and the mixture was shaken to form a slightly yellowish, homogeneous solution. A polypropylene plastic dish was used as a casting mold for the repellent/polymer solution. The solution was poured into the mold/dish forming a flat sheet on the bottom of the mold. The dichloromethane was allowed to evaporate overnight and the final composition formed a dry film on the bottom of the mold that contained about 50% by weight methyl nonyl ketone.

Seven days after the fabrication of a controlled release device described above, the device was partially filled with bird seed which contained sunflower seeds in their shells. A control dish containing no repellent was also partially filled with sunflower seeds. The containers were attached to wooden boards and placed ten feet apart in an area which had been observed to attract significant numbers of squirrels, raccoons and birds. The temperature during the 24 hour test period ranged from 39° F. to 60° F., with no precipitation and about 40% humidity. The test period was sunny for most of the daylight hours.

After 24 hours, the contents of the control container showed signs of animal use. Most nut-type sunflower seeds were gone. Seed husks were littered on the ground adjacent to the control container. The wooden board had been moved from its original position. In contrast, the repellent device showed no signs of having been touched by animals. Nut-type sunflower seeds were still in the device and no husks were around the device. The wooden board remained in its original position. Thus, the device described above repelled animals up to at least seven (7) days after fabrication.

Example 2

Evaluation of Release of Repellent as a Function of Percent Loading

Repellent devices were fabricated with varying quantities of an active repellent, methyl nonyl ketone, in order to demonstrate the sustained release of the repellent over a 68 day period. The devices were fabricated as described in Example 1, with varying quantities of methyl nonyl ketone as outlined in Table I. The solutions were cast into 5 cm diameter polypropylene caps and allowed to dry overnight.

TABLE I

Fabrication variables of methyl nonyl ketone test films and controls.

| methyl nonyl ketone (grams) | 10% (wt/wt) EVAc/ $CH_2Cl_2$ (grams) | methyl nonyl ketone (wt % w. EVAc) | $CH_2Cl_2$ (grams) |
| --- | --- | --- | --- |
| 0.510 | 20.69 | 20 | 0 |
| 1.000 | 22.53 | 31 | 0 |
| 2.001 | 20.84 | 49 | 0 |
| 2.010 | 0 | 100 | 19.44 |
| 2.000 | 10 | 100 | 0 |

The release of the methyl nonyl ketone was determined by measuring the decrease in weight of the films using an analytical balance (Mettler-Toledo model 302) over 68 days. The release kinetics are graphed in FIG. 1 as the cumulative mg of methyl nonyl ketone released over the time period.

The data demonstrates the sustained release of the repellent over a 68 day time period and the ability to control the amount released over time by varying the loading of the EVAc matrices. Increasing the weight percent loading of the methyl nonyl ketone in the matrix resulted in larger quantities of nonyl methyl ketone released. The control devices (the last two entries in the table) demonstrate that the addition of $CH_2Cl_2$ to methyl nonyl ketone exhibited no effect on release as compared to the control containing no $CH_2Cl_2$.

The device therefore continuously releases the repellent while protecting dilution of the repellent due to environmental forces such as rain, snow, wind and runoff. The device also allows the concentration of effective quantities of methyl nonyl ketone in safe and easy to handle polymeric devices for use in the continuous repelling of nuisance animals.

Example 3

Use of Devices to Repel Other Animals

Repellent delivery devices prepared as in Example 1 above were prepared and attached to a garbage bag filled with decomposing food stuffs including fruit rinds, proteins and vegetables. The bag was left out overnight in an area known to be frequented by raccoons and other animals. After 2 days in an unprotected environment, the bag remained intact. It did contain some holes, presumably introduced by animals which tried to enter the bag but which were repelled by the continuous delivery of methyl nonyl ketone from the delivery devices.

Animal repellent devices prepared as described in Example 1 were placed in a vegetable garden containing several tomato plants that was regularly violated by squirrels and other small animals. The small animals ceased from disturbing the vegetable garden for several weeks.

Animal repellent devices prepared as described in Example 1 were placed on a house deck known to be frequented by raccoons, attached with a string to the outside of a 30 gallon garbage container. The garbage container remained outside for two weeks and overturning and disruption of the garbage container ceased. After the two week test period, the repellent devices were removed and the garbage container not protected by the repellent devices was found overturned and garbage was strewn about the surrounding area on the morning following the removal of the repellent device.

These results indicate that these devices effectively protect an area in a safe and effective manner over an extended time period.

Example 4

Device Containing Animal Predator Urine 4.53 grams of coyote urine was combined with 0.63 grams of L101 Pluronic. 50 grams of 10% EVAc dissolved in dichloromethane (wt/vol) was then mixed with the coyote urine and L101 Pluronic solution. The mixture was vigorously shaken, forming a dispersion of the coyote urine within the polymer solution. The dispersion was then cast into a 6 inch by 8 inch aluminum pan and allowed to dry into a film overnight.

The aluminum backed film was cut into strips approximately 1.5 inches wide by 6 inches long. The film strips were affixed to various points in the front and back yard of a home being frequented by skunks and raccoons. The strips remained on the property over a 2 month period.

The raccoons ceased to disrupt the garbage cans of the home for the first time in several months over the two month test period. The skunks also ceased to release their offensive odors in and around the home.

These results indicate that the sustained release of the coyote urine from these polymer matrices controlled and prevented raccoons and skunks from frequenting this household and its surroundings.

Example 5

Device Containing Animal Predator Urine 10 grams of coyote urine was dispersed in 100 ml of a 10% (wt/vol.) solution of ethylene vinyl acetate copolymer dissolved in dichloromethane. The solution was shaken vigorously and then cast into molds. The molds were pre-cooled to insure homogeneous distribution of the aqueous urine solutions. In a alternate embodiment of the device, the predator urine can be dried by methods such as freeze drying to remove the water contained in urine. The remaining solid material can be incorporated into the device by dispersing the dried urine material in a 10% (wt/vol.) solution of ethylene vinyl acetate copolymer dissolved in dichloromethane. The suspension can then be cast into molds. Both methods will yield a thin polymer film, which is placed in areas where animals such as squirrels, mice, deer etc. are troublesome.

Example 6

Aqueous Based Modified Food Starch Film Containing Bobcat or Coyote Predator Urine It may be desirable in some cases to incorporate water soluble repellents into aqueous based polymer films. In order to accomplish this, 75.3 grams of pure Cote B790 modified food starch was dispersed in 150 ml cold water. The suspension was heated to 82° C. and held at that temperature for 12 minutes. The suspension turned to a translucent solution, which is a hydrated starch slurry. 50 ml of the slurry was cast into a plastic mold containing 10 ml of bobcat or coyote urine and allowed to dry overnight. The resulting dried composition could be used as a repellent device.

The teachings of the references cited herein are specifically incorporated herein. Modifications and variations of the present invention will be obvious to those skilled in the art from the foregoing detailed description and are intended to be encompassed by the following claims.

What is claimed is:

1. A method of repelling a raccoon from an area or object, the method comprising obtaining a repellant composition comprising methyl nonyl ketone and a polymer matrix, wherein the methyl nonyl ketone is dispersed within the polymer to form a sustained-release repellant composition, and wherein the polymer comprises ethyl vinyl acetate, polyethylene, polypropylene, polyvinyl chloride, a polyester, a polyorthoester, a polyurethane, polystyrene, a polyanhydride, a polycarbonate, polyvinyl acetate, or copolymers or mixtures thereof; and applying the sustained-release repellant composition in the area or on or near the object from which the raccoon is to be repelled.

2. The method of claim 1, wherein the polymer matrix comprises a sheet, film, a shaped article, or a pellet.

3. The method of claim 1, wherein the object is a garbage can or refuse receptacle.

* * * * *